United States Patent [19]

Trofimov et al.

[11] Patent Number: 5,198,552

[45] Date of Patent: Mar. 30, 1993

[54] INDOLE DERIVATIVE HAVING ANTIVIRAL, INTERFERON-INDUCING AND IMMUNOMODULATORY EFFECTS

[76] Inventors: Fedor A. Trofimov, prospekt Marxa, 28, Kv. 36, Kaluzhskaya oblast, Obninsk; Nina G. Tsyshkova, prospekt Marxa, 54, Kv. 17, Kaluzhskaya oblast, Obninsk; Nadezda S. Bogdanova, ulitsa 26, Bakinskikh Kommisarov, 1 Korpus 1, Kv. 26; Irina S. Nikolaeva, ulitsa Matveevskaya, 1, Kv.; Svetlana A. Zotova, pereulok Obukha, 4, Kv. 85; Zinaida M. Sakhaschik, ulitsa Sheremetievskaya, 5, Korpus 2, Kv. 44; Elena N. Padeiskaya, Leninsky prospekt, 13, Kv.; Alla N. Fomina, ulitsa Belomorskaya, 8, Kv. 2, all of Moscow; Evgenia H. Svirina, Moskovskaya oblast, Klimovsk- 3; Dmitry M. Zlydnikov, Nevsky prospekt, 66, Kv.; Olga I. Kubar, ulitsa Avtovskaya, 2, Kv. 102; Evgenia G. Shvetsova, Zamshina, 25 Korpus 4, Kv. 61; all of Leningrad; Svetlana N. Kutchak, ulitsa Tsjurupy, 13, Kv. 68; Valentina V. Peters, ulitsa Losevskaya, 22, Kv. 32, both of Moscow; Elena A. Bryantseva, prospekt Kima, 28, Kv. 275, Leningrad; Anatoly G. Konoplyannikov, prospekt Lenina, 1, Kv. 62; Boris P. Surinov, prospekt Lenina, 90, Kv.; Vera A. Yadrovskaya, ulitsa Axenova, 7, Kv. 98; all of Kaluzhskaya oblast, Obninsk; Ljudmila S. Satonova, ulitsa Sofii Kovalevskoi, 5 Korpus 7, Kv. 89; Leningrad; Nina A. Karpova, ulitsa Marshala Zhukova, 12, Kv. 56; Elena P. Savina, ulitsa Koroleva, 27, Kv. 139, both of Kaluzhskaya oblast, Obninsk; Ljudmila A. Savinova, ulitsa Tipanova, 6, Kv. 62, Leningrad; Alexei N. Grinev, deceased, late of Moscow, administrator; by Galina V.; Grineva, ulitsa Koshtoyantsa, 21A, Kv. 33, Moscow; Grigory N. Pershin, deceased, late of Moscow, administrator; by Ellina G. Pershina, ulitsa 26, Bakinskikn, Komissarov 8, Korpus 4, Kv. 93, Moscow, all of U.S.S.R.

[21] Appl. No.: 576,444

[22] PCT Filed: Jan. 12, 1989

[86] PCT No.: PCT/SU89/00272

§ 371 Date: Nov. 12, 1991

§ 102(e) Date: Nov. 12, 1991

[87] PCT Pub. No.: WO90/08135

PCT Pub. Date: Jul. 26, 1990

[51] Int. Cl.[5] .................................... A61K 31/405
[52] U.S. Cl. .................................... 548/492; 548/502
[58] Field of Search ................. 548/492, 502; 514/419

[56] References Cited

U.S. PATENT DOCUMENTS

| | | | |
|---|---|---|---|
| 4,124,702 | 11/1978 | Lampson et al. | 424/85 |
| 4,215,137 | 7/1980 | Dobson et al. | 424/274 |
| 4,619,942 | 10/1986 | Tidwell et al. | 514/415 |

FOREIGN PATENT DOCUMENTS

WO87/06227 10/1987 Netherlands.
WO90/08135 7/1990 U.S.S.R..

*Primary Examiner*—David B. Springer
*Attorney, Agent, or Firm*—Burgess, Ryan & Wayne;

[57] ABSTRACT

A novel compound—ethyl 6-bromo-5-hydroxy-4-dimethylaminomethyl-1-methyl-2-phenylthiomethylindole-3- carboxylate hydrochloride monohydrate having the following formula:

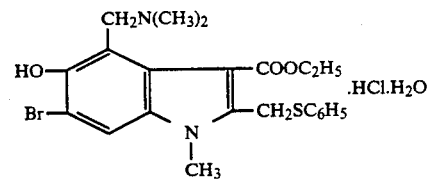

A process for preparing the compound according to the invention, characterized in that it comprises treating ethyl 5-acetoxy-1,2-dimethylindole-3-carboxylate with a brominating agent in an inert organic solvent under reflux, reacting the resultant ethyl 5-acetoxy-6-bromo-2-bromomethyl-1-methylindole-3-carboxylate with thiophenol in the presence of an alkali metal hydroxide or its alcoholate in an organic solvent, reacting the resultant ethyl 6-bromo-5-hydroxy-1-methyl-2-phenylthiomethylindole-3-carboxylate with an aminomethylating agent in an organic solvent at a temperature of from 65° C. to a temperature of refluxing the reaction mixture. The end product is then isolated from the resultant base—ethyl 6-bromo-5-hydroxy-4-dimethylaminomethyl-1-methyl-2-phenylthiomethylindole-3- carboxylate.

The compound according to the invention is an active principle of a pharmaceutical preparation having the antiviral, interferon-inducing and immunomodulatory effects.

12 Claims, No Drawings

INDOLE DERIVATIVE HAVING ANTIVIRAL, INTERFERON-INDUCING AND IMMUNOMODULATORY EFFECTS

TECHNICAL FIELD

The present invention is in the field of organic chemistry, and more particularly it relates to a novel compound—ethyl 6-bromo-5-hydroxy-4-dimethylaminomethyl-1-methyl-2-phenylthiomethylindole-3-carboxylate hydrochloride monohydrate, a process for preparing thereof, and a pharmaceutical preparation containing the same having the antiviral, interferon-inducing and immunomodulatory effects.

BACKGROUND ART

Nowadays, much consideration is given to a search for and a study for of antiviral, interferon-inducing and immunomodulatory agents. A special attention focuses on agents which are capable of modulating, potentiating or inhibiting a body's immune reactions—immunomodulators.

Immunomodulator increase a general body resistance effecting specific immune reactions and nonspecific defensive factors including an endogenous interferon production. They are used for treating diseases in pathogenic mechanisms of which disorders of a body immune status play an important role—primary and secondary immunodeficiency conditions including cancers as well as chronic and relapsing virus infections.

Among a few synthetic chemicals used as immunomodulators the most effective and widely used in the clinical practice is levamisole/(−) 2,3,5,6,-tetrahydro-6-phenylimidazo-/2.1.b/-thiazole hydrochloride/. /A.D. Mashkobsky, Lekarstvennye sredstva, 1987, (Mosk\*a), "Meditsina", v. 2, pp. 169-171/.

Levamisile as an immunomodulator is used in a complex therapy of various diseases associated with immunodeficiency conditions. The use of levamisole for treating severe retroforms of herpes virus infection is disclosed in literature. Levamisole as well as some other immunomodulators stimulates the production of serum interferon in the body. The interferon titers, produces by the action of levamisole are not over 80–160 U/ml in a cell culture; 160–320 U/ml in the mouse blood serum and 40–80 U/ml in the human blood serum.

However, levamisole is highly toxic and may cause various side-effects; a headache, sleep disturbances, olfactory hallicinations (odour changes), allergic skin hypersensitivity, influenza-like and neurologic symptoms.

The most prejudicible side-effect which may take place in the treatment by using levamisole as an immunomodulator is agranulocytosis—the decrease of neutrophile to a value below 25%. Therefore, the blood should be systematically assayed during the treatment with levamisole.

At present, antiviral drug preparations are also known to contain adamantane derivatives as an active principle, for example, remantadine (alfa-methyl-1-adamantanemethylamine hydrochloride)/Mekhanizmy antivirusnogo deistvia proizvodnykh adamantana, 1982, (Riga) "Zinatne", pp. 25-29, 129-141/. These preparations have a side-effect on a central nervous system.

SUMMARY OF THE INVENTION

The compounds according to the invention, a process for preparing thereof, and a pharmaceutical preparation containing the same are novel and they have not been reported.

The invention is based on the problem of providing a novel compound having high antiviral, interferon-inducing and immunomodulatory effects, a low toxicity, no side-effects, and a process for preparing thereof.

This problem is solved by providing a new compound—ethyl 6-bromo-5-hydroxy-4-dimethylaminomethyl-1-methyl-2-phenylthiomethylindole-3-carboxylate hydrochloride monohydrate according to the invention of the following formula:

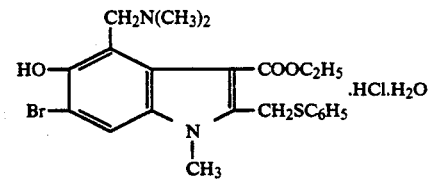

The compound according to the invention is a crystalline powder, having a colour from white with tints of green-yellow to light-yellow with green hues; a bitter in taste, odourless. The melting point of the compound is not characteristic. When heated for 3 hours at a temperature ranging from 110° to 120° C., it looses the molecule of $H_2O$.

The compound of the invention is poorly soluble in water, methanol, ethanol, non-hydroscopic. The solution containing 1 g of the compound in 1450 ml of water at 25° C. has pH of 4.37 (potentiometrically).

The UV spectrum of a 0.001% solution of the compound of the invention in 95M ethanol in the region of 230 nm to 350 nm has two absorption peaks at 257±2 nm (lg$\epsilon$ 4.3), and at 315±3 nm (lg$\epsilon$ 3.2). The IR spectrum has absorption bands at 3320 cm (OH-group) and 1673 cm$^{-1}$ (C=O-group).

In the mass-spectrum low-intensivity peaks with m/z of 476/478, belonging to a molecular ion are observed. The ratio of peak intensities $J_{476}:J_{478}$ corresponds to the presence of one bromine atom in the molecule. The spectrum is characterized by intensive peaks of ions/M-Ph SH/+ (m/z 322/324), PhSH+ (m/s 110), m/z 44 ($CO_2$). The mass spectrum is unstable because heating of the sample results in its thermal decomposition.

According to the invention, a process for preparing the compound of the invention—ethyl 6-bromo-5-hydroxy-4-dimethylaminomethyl-1-methyl-2-phenylthiomethylindole-3-carboxylate hydrochloride monohydrate is characterized in that it comprises treating ethyl 5-acetoxy-1,2-dimethylindole-3-carboxylate with a brominating agent in an inert organic solvent under reflux, reacting the resultant ethyl 5-acetoxy-6-bromo-2-bromomethyl-1-methylindole-3-carboxylate with thiophenol in the presence of an alkali metal hydroxide or alcoholate, reacting the resultant ethyl 6-bromo-5-hydroxy-1-methyl-2-phenylthiomethilindole-3-carboxylate with an aminomethylating agent in an organic solvent at a temperature from 65° C. to a temperature of refluxing the reaction mixture and then isolating the end product from the resultant base—ethyl 6-bromo-5-hydroxy-4-dimethylaminomethyl-1-methyl-2-phenylthiomethylindole-3-carboxylate.

A brominating agent is preferably bromine or N-bromosuccinimide, and an inert organic solvent is chloroform, dichloroethane or tetrachloromethane. In the reaction of ethyl 5-acetoxy-6-bromo-2-bromomethyl-1- methylindole-3-carboxylate with thiophenol an organic solvent is preferably methanol and ethanol or isopropanol.

As aminomethylating agent is preferably used a mixture of dimethylamine with formaline or bis-dimethyl aminomethane.

When a mixture of dimethylamine and formaline is used, an organic solvent is acetic acid, and the aminomethylation is carried out at a temperature in the range of 65° to 75° C.

When bis-dimethylaminomethane is used as an aminomethylating agent, a preferable organic solvent is dioxane and the aminomethylation is preferably carried out at a temperature of refluxing the reaction mixture.

The isolation of the end product is preferably carried out by treating ethyl 6-bromo-5-hydroxy-4-dimethylaminomethyl-1-methyl-2-phenylthiomethylindole-3-carboxylate with hydrochloric acid in acetone under reflux.

The yield of the end product based on the starting ethyl 5-acetoxy-1,2-dimethylindole-3-carboxylate is of 44 to 61% by mass.

The compound of the invention has the antiviral, interferon-inducing and immunomodulatory effect, and, according to the invention, it is an active principle of a pharmaceutical preparation, having an antiviral, interferon-inducing and immunomodulatory effect. The preparation of the invention may be used in various forms, preferably as tablets.

According to the invention the preparation of the invention in the form of tablets contains an active principle in an amount of 0.1 to 0.2 g per one tablet. As a pharmaceutical carrier the preparation of the invention preferably contains an excipient—starch or castor sugar.

BEST MODE TO CARRY OUT THE INVENTION

The preparation of the invention was studied in an animal test and clinically on human beings. The antiviral effect of the preparation against influenza A/B viruses was tested on a hen embryo fabroblast cell culture.

The preparation of the invention was added to a well culture in the amount of 5 μm/ml in different periods before and after infecting the culture with influenza viruses to study the effect of the preparation on accumulation of an infectious virus in a tissue cell culture during a single-stage infection.

In another series of experiments the effect of the preparation of the invention on influenza virus reproduction depending on the time of adding the preparation before and after infection of a cell culture, in other words on the dynamics of influenza virus reproduction, was tested.

The results of experiments showed that the virus-inhibiting effect in reducing the infectivity titer and suppressing the plague-forming activity during a single-stage infection of cells of the preparation of the invention was expressed mainly during periods, corresponding to early stages of influenza viruses reproduction in cells: adsorption, penetration and probably deproteinization.

The antiviral effect of the preparation of the invention was studied as compared to a known drug—remantadine.

The preparation of the invention is superior over remantadine as regards a wide antiviral spectrum, shows a pronounced chemotherapeutical effect against influenza A/B viruses in a cell culture and on an experimental influenzal pneumonia, induced by A/B viruses. Remantadine is efficient only against influenza A virus, but it is inefficient against influenza B virus. In addition, in the experiment, the resistivity of influenza viruses to the preparation develops much slower as compared to remantadine.

A comparative characteristic of the antiviral activities of the preparation according to the invention and remantadine is given in Table 1.

The experimental study of harmfulness of the preparation according to the invention showed that the preparation in a single oral administration was low toxic ($LD_{50}$ for mice is of 340 mg/kg, for rats—3.000 mg/kg, for guinea pigs —4.000 mg/kg).

A long-term per os administration of the preparation of the invention in a dose of 100 to 125 mg/kg to rats during 6 months and guinea pigs over 3 months, in the dose of 50 mg/kg during 2 months to rabbits and in the dose of 25 mg/kg over 6 months to dogs did not cause any pathological changes in animals which is supported by a clinical, hematological, biochemical and pathomorphological evidence. A prolonged administration of the preparation may cause in animals the development of non-specific degenerative alternations in parenchymatous organs. The preparation of the invention has no localized irritant action in oral administration which is evidenced by hystological tests.

TABLE 1

| The preparation or the invention | Remantadine |
|---|---|
| Inhibits the reproduction of influenza A/B viruses in a cell culture and chick embryos. | Inhibits the reproduction of influenza A/B viruses in a cell culture and chick embryos. It is inefficient against virus B. |
| Exerts a medicinal effect on an influenzal mice pneumonia induced by influenza A/B viruses. In passivating the influenza A virus in a cell culture in the presence of the preparation during 6 passes there is no virus resistance to the preparation. | Exert a medicinal effect on an influenzal mice pneumonia induced by influenza A/B viruses. In passivating the influenza A virus in a cell culture in the presence of remantadine there occur the resistance to the preparation beginning from a 2-3 passes. |
| No virucidal action on influenza viruses. The maximum tolerable concentration for a cell culture - chick embrio fibroblasts - 20 μg/ml. $LD_{50}$ for mice 340 mg/kg with per os administrating. | No virucidal action on influenza viruses. The maximum tolerable concentration for a cell culture - chick embryo fibroblasts - 20 μg/ml. $LD_{50}$ for mice 340 mg/kg with per os administrating. |

The allergizing effect of the preparation of the invention was tested on guinea pigs and rabbits. In carrying out subcutaneous injections and repeated skin applications, the preparation did not exert an allergizing action.

The preparation of the invention has no teratogenic activity. In a non-toxic dose of 250 mg/kg for pregnant female animals (20–30 times as high as a maximum human daily dose) the preparation did not cause abnormalities in embryogenesis as well as in a postnatal development of albino rats. A complex analysis of an embryo state and the descent of the first generation, using microanatomical, histological, physiological, and behavioral tests was accomplished.

The preparation of the invention has no mutagenic activity. The study was carried out on the test object *Salmonella typhimurium* using the preparation of the invention in a amount of 50 to 1000 μm per disk.

The preparation of the invention passed a clinical trials as an antiviral drug agent for influenza A/B virus infection on 1650 patients.

The preparation of the invention was administered orally in the dose of 0.2 g 4 times a day during 3 days. The clinical checking of the preparation was performed in comparison to control groups o patients which were taken a symptomatic treatment. The Therapeutical efficacy of the preparation of the invention against an influenza A/B virus infection was manifest by shortening the febrile period, intoxication and catarrhal conditions as well as by shortening the illness duration. A medicinal efficacy of the preparation of the invention was evidenced by data of serological tests—an incremental ratio of antibodies to influenza A/B viruses significantly decreased as compared to control groups of patients given a symptomatic treatment. The preparation of the invention prevented the development of postinfluenzal complications and decreased considerably the frequency of chronic disease exacerbations in human beings who has an influenza virus infection.

The clinical trials have proven a safety of the preparation in application in doses of 1800 to 3200 mg per course; side-effects occurred neither in influenzal patients nor in healthy individuals volunteers.

The study of the interferon-inducing effect of the preparation of the invention was carried out in experiments in vitro (on an initially trypsinized cell culture of hen embryo fibroblasts), in experiments in vitro on 340 noninbred albino mice weighing from 18 to 20 g, and on 25 volunteers (healthy young individuals of both sexes at the age of 18 to 30).

In order to induce interferon, different doses of the preparation of the invention together with 2% diethylaminoethyl dextran in a 1:4 ratio were added to a hen embryo fibroblast cell culture in 0.2 ml per tube contained a cell culture monolayer. The incubation of treated cells was carried out at 37° C. for 1 hour. The cells were then rinsed from the preparation with the medium No. 199, and 1 ml of the medium No. 199 was poured therein without adding the bovine blood serum. In 8, 24 and 48 hours after the incubation at 37° C. a culture fluid was collected and titrated in the presence of interferon in a hen embryo fibroblast cell culture infected with *Venezuelan encephalitis* viruses using a conventional technique.

The results of titration are given in Table 2.

In studying the interferon-inducing effect of arbidole a reference standard was a highly active interferon inducer—a double-stranded $RF_2$ phage RNA (a double-stranded ribonucleic acid of $RF_2$-phage).

The results given in Table 2 allow the conclusion that the preparation of the invention is a highly active interferon inducer in a hen embryo fibroblast cell culture. At the concentration of 20 g/ml the preparation induces interferon already in 8 hours (its titer 640–1280 U/ml; the maximum titer of 2560 U/ml was found 24 hours later; by 48 hours the interferon titer decreases to 320 U/ml).

A dose-dependent effect of interferon induction in a hen embryo fibroblast cell culture under the action of the preparation was established. A two-fold reduction of the concentration of the preparation (up to 10 μg/ml) leads to an 8-fold reduction of interferon induction, the dynamics, however, remains the same.

TABLE 2

Interferon-Inducing Effect of the Preparation According to the Invention in a hen Embryo Fibroblast Cell Culture

| Preparation | Concentration | Interferon titer (lg/ml) after | | |
|---|---|---|---|---|
| | | 8 h | 24 h | 48 h |
| The preparation of the invention | 10.0 | 80.0 | 160.0 | 40.0 |
| The preparation of the invention | 20.0 | 640–1280 | 1280–2560 | 64–320 |
| A double-stranded $RF_2$-phage RNA | 100.0 | 0 | 160.0 | not studied |
| A double-stranded $RF_2$-phage RNA | 400.0 | 640–1280 | 1280–2560 | 640–320 |

A comparative study of interferon induction by the action of the preparation of the invention and a double-stranded $RF_2$-phage RNA as a highly active interferon inducer standard revealed a similar induction dynamics, whereas a double-stranded $RF_2$ phage RNA was needed 20 times as much as the preparation (400 g/ml), the concentration of 100 g/ml caused a weak (slight) interferon induction.

In the following series of experiments the capability of the preparation of the invention to induce interferon in test animal blood serum was studied.

The preparation of the invention was per os administered once to mice (3 mouse groups each of 100 animals in the doses of 250, 125 and 62.5 mg/kg, and 16, 24, 48 and 72 hours later blood serum was obtained to be used for interferon titrations in a transferred mouse L-cell line against test vesicular stomatitis viruses. In addition, the preparation of the invention was once injected intraperitoneally into the group of 20 mice in the dose of 10 mg/kg, and 24 hours later blood serum was obtained in which interferon titres were also determined.

The experimental results are given in Table 3.

TABLE 3

Dynamics of Interferon Induction under the Action of the Preparation of the Invention

| Preparation and administration method | Dose, mg/kg | Interferon titer (U/ml) after | | | |
|---|---|---|---|---|---|
| | | 16 h | 24 h | 48 h | 72 h |
| The preparation of the invention (per os) | 250 | 320–540 | 640–1280 | 320 | 160 |
| The preparation of the invention (per os) | 125 | 640 | 320–640 | 640 | 160 |
| The preparation of the invention (per os) | 62.5 | 320–640 | 640 | 160 | 40 |
| The preparation of the invention (intraperitoneally) | 10 | not studied | 640–120 | not studied | |
| Mice blood serum without the preparation of the invention | 0 | 10–20 | 10–20 | 10–20 | 10–20 |

The results presented in Table 3 show that the preparation of the invention administered per os causes interferon induction in the mouse blood serum. The effect is characterized by dose-dependence and is most strong by pronounced in a dosage range of 250 to 62.5 mg per 1 kg of an animal body weight. High interferon titers (640 U/ml) were found in the mouse blood serum in 16 hours, and persisted there during up to 48 hours. The preparation of this invention enhances the interferon induction also in case of intraperitoneal injection.

With repeated administering of the preparation of the invention to mice for interferon induction, a depressed reactivity state condition occurs in the animals, which is pronounced in reducing the interferon titers in the blood serum.

The preparation of the invention as an interferon inducer has a preventive effect on induced virus infections. Its preventive effect was studied on a mouse influenzal pneumonia induced by infecting the animals intranasally with influenza A virus (Bethezda) 63 ($H_2N_2$), A (Aichi) ($H_3N_2$) and on a generalized mouse herpes, induced by intranasal infection of them with herpes simplex virus from antigen-type I $L_2$-strain.

The results are given in Table 4.

The preparation of the invention in administering it per os as prophylactic 24 and 6 hours before infecting in doses of 31.2 mg/kg to 125 mg/kg lowers lethality of mice suffering from an influenzal pneumonia by 40-50% as compared to control. A single administration of the preparation per os in the dose of 30 mg/kg 24 hours prior to infection prevents the death of 40% of animals suffering from a generalized herpetic infection.

assayed for serum interferon. Serum titration was performed with conventional procedures using a human diploid M-22 cell culture and test mouse encephalomyocarditis viruses. The results are given in Table 5.

TABLE 5

Study of Interferon-inducing Effect of the Preparation of the Invention in Human Beings

| | | Interferon content in the human blood serum | | | | | |
|---|---|---|---|---|---|---|---|
| | | After a single administration of the preparation on the invention per day (100 mg) | | After administering the preparation 3 times per day (300 mg) | | After administering the preparation of the invention 6 times per day during 2 days (600 mg) | |
| No. group | The number of men in group | The number of positive reactions | Inteferon titer, U/ml | The number of positive reactions | Interferon titer, U/ml | The number of positive reactions | Interferon titer, U/ml |
| Group 1 | 13 | 8 | 40-80 | — | — | — | — |
| Group 2 | 12 | — | — | 12 | 160-320 | 12 | 40-80 |

It has been found that a single per os administration of the preparation of the invention in the amount of 100 mg causes the interferon induction in titers ranged of 40 to 80 U/ml in 8 out of 13 volunteers (61.5%). A 3-times administration of the preparation (300 mg) 1 tablet a day resulted in a rapid decrease of interferon induction (interferon was found in the blood serum in all 12 volunteers (100%) in titers contained 160-320 U/ml. With a further increase in the dose to 600 mg (3 tablets a day) during 2 days, a sharp reduction of interferon induction occurred (the interferon titer in the blood serum was not in excess of 40-80 U/ml).

The results obtained show a pronounced interferon-inducing effect of the preparation of the invention in human beings in administering it per os. Maximum content of interferon in the human blood serum was found after administration of 300 mg of the preparation of the invention (in 100 mg 3 times a day). An increase in the dose and duration of administration of the preparation resulted in the development of hyporeactivity in human beings, which was characterized by a sharp reduction of serum interferon titers.

The immunomodulatory immunopotentiating effect of the preparation of the invention was also assayed.

The effect of the preparation of the invention on the immune system functions was studied.

Phagocyte function under the action of the preparation of the invention was studied on adult female hybridous mice (CBA/C 57 $Bl_6$)F.

The preparation of the invention was administered per os in the dose of 125 mg/kg once and once in a day during 5 days. A reference standard was levamisole given on the same scheme in the dose of 50 g per mouse. During different period after administering of the preparation mouse peritoneal macrophages were isolated in which an absorbing capacity was measured by absorbance of neutral red and was determined quantitatively from a calibration curve using spectrophotometrical techniques (at 530 nm).

The results are given in Table 6.

The administration of the preparation according to the invention and levamisole has no effect on counts of macrophages washed off the peritoneal cavity, but it enhanced their absorbing (activity) capacity. Thus, by 2-3 days after a single administration of the preparation the absorbing capacity of macrophages was remained at the same level—164±13% (p<0.05) and 138±11% (p<0.05), respectively.

TABLE 4

Preventive Action of the Preparation According to the Invention in Experimental Virus Infections Mouse influenzal pneumonia

| Dose, mg/kg | Time and administration method | Lethality: absolute animal number, (*) | % | The decrease of lethality, % | P |
|---|---|---|---|---|---|
| 1 | 2 | 3 | 4 | 5 | 6 |
| 125 | per os | 8/40 | 20 | 50 | <0.01 |
| 62.5 | 24 and | 8/40 | 20 | 50 | <0.01 |
| 31.2 | 6 hours before infecting | 12/40 | 30 | 40 | <0.01 |
| Control (without the preparation | | 28/40 | 70 | — | |
| 30 | per os, | 12/20 | 60 | 40 | 0.01 |
| 15 | 24 hours | 15/20 | 75 | 25 | 0.01 |
| Control (without the preparation) | | 20/20 | 100 | — | |

*in the numerator - the number of dead animals
in the denominator - the number of mice in the group The interferon-inducing effect of the preparation of the invention was studied also in human beings. The blood serum of human beings give per os tablets of the preparation (0.1 g) in different dosage schemes were

TABLE 6

Absorbing Capacity (mg/6 × 10⁶ cells) of Peritoneal Macrophages during Different Periods after a Single Administration of the Preparation of the Invention and Levamisole

| Time after administration | Control (starch) | Levamisole | The preparation of the invention |
|---|---|---|---|
| The 1 day | 20.8 ± 3.8 | 24.2 ± 4.5 (116 ± 21%) | 27.7 ± 3.5 (125 ± 17%) $p < 0.01$ |
| The 2 day | 22.8 ± 2.0 | 27.7 ± 3.2 (121 ± 14%) | 33.6 ± 4.7 (147 ± 20.6%) $p < 0.05$ |
| The 3 day | 24.1 ± 4.2 | 32.5 ± 2.4 (135 ± 9.9%) | 37.4 ± 3.7 (155 ± 15%) $p < 0.05$ |

Note:
in brackets percent of control.

Thus, administering the preparation of the invention in vivo stimulates the absorbing capacity of macrophages to a greater extent than administration of levamisole.

The effect of the preparation of the invention on antibody genesis was studied in comparison with levamisole and a double-stranded $RF_2$ phage RNA. There were used hybrid mice (CBA/A 57 BL₆)F as well as the tumor-carrier animals (breast cancer grafted subcutaneously into a leg), intact and totally irradiated (2 Gr.).

The antibody-producing mechanism was studied as applied to sheep erythrocytes by subperitoneal immunization of the animals in the amount of 1×10⁸ cells. Five days after immunization the animals were sacrificed by decapitation, and the content of antibody-producing cells in the spleen was determined according to Canningame. The results of the tests are summarized in Table 7.

The preparation of the invention increased the content of antibody-producing cells at different dosage schemes up to 167–246%, and levamisole and a double-stranded $RF_2$ phage RNA, in the range of 143 to 170%.

Only the preparation of the invention had a pronounced immunostimulating effect on irradiated animals, and to a maximum degree when administered 3 days prior to irradiation: once irradiated, the immune response was of 230% against the control. Levamisole was of low efficacy in these animals; a double-stranded $RF_2$ phage RNA was inefficient.

TABLE 7

Comparative Study of Effects of the Preparation of the Invention, Levamisole and a Double-Stranded $RF_2$ Phage RNA on Antivody-Producing Mechanism (% of control) in intact mice, totally irradiated (2 Gr.), tumor-carriers and totally irradiated tumor-carriers (2 Gr.)

| Animal groups (mice) | Levamisole during 3 days, daily | Levamisole 5 times at a 5-day interval | A double-stranded $RF_2$ phage at a 3-day interval |
|---|---|---|---|
| 1 | 2 | 3 | 4 |
| Intact | 164 ± 6.1 | 170 ± 15.1* | 143 ± 7.5 |
| Totally irradiated (2 Gr.) | 174 ± 24.0 | 104 ± 6.0 | 80 ± 6.6 |
| Tumor-carriers | 14 ± 23.0 | 91 ± 14.0 | 74 ± 31.0 |
| Irradiated | 86.0 ± 35.0 | 402 ± 12.5 | 92 ± 21.0 |

| The preparation | The preparation of the invention; a single use 5 | The preparation of the invention during 3 days, daily 6 | The preparation of the invention during 5, daily 7 | The preparation of the invention 5 times in 3 days 8 |
|---|---|---|---|---|
| | 246 ± 6.0* | 141 ± 13 | 192 ± 14.0* | 167 ± 12.3* |
| | 230 ± 12.0* | 129 ± 19 | 181 ± 11.3 | 96 ± 20.0 |
| | 211 ± 10.0* | 99 ± 19 | 154 ± 16.6* | 110 ± 11.0 |
| | 175 ± 24.6* | 121 ± 25 | 128 ± 28.5 | 250 ± 21.5* |

Note:
*Differences from control values are confident ($p < 0.05$).

The preparation of the invention has also the immunopotentiating effect on tumor-carrier animals (the 7–17 day of tumor development) after a single (3 days prior to immunization) or a 5-times daily administration. Levamisole and a double-stranded $RF_2$ RNA in these experiments were inefficient.

The preparation of the invention was active only in totally irradiated tumor-carrier animals and had a pronounced immunopotentiating effect even in cases when the level was decreased to about 50 times as low as compared to intact animals. Levamisole also had the immunopotentiating effect on these animals; a double-stranded $RF_2$ phage RNA was inefficient.

Thus, the preparation of the invention is capable of stimulating (enhancing) the antibody genesis in all mouse breeds tested, both intact and irradiated, and by efficiency it is superior over reference standards—levamisole and a double-stranded $RF_2$ phage RNA.

The effect of the preparation of the invention on cell-mediated immunity responses was studied using the graft versus host technique.

Hybridous male mice (CBA/C 57 BL₆)F₁ at the age of 3 months were irradiated in the dose of 5 Gr. One day after irradiation the animals were given injections intravenously with lymphocytes prepared from lymphadens of a parent mouse CBA breed aged 3 months, in the concentrations of 1.25, 2.5 and 5.0×10⁶ kariocytes. Once lymphocytes were intravenously injected in the test groups, the preparation of the invention was administered orally in a dose of 100 mg per 1 kg of a body weight, and levamisole in a dose of 5 mg per 1 kg in a 2% starch solution. Each group had 15 mice. Eight days after irradiation the mice were killed, the spleens were fixed, and the count of colonies having a diameter of at least 0.2 mm was determined.

The data obtained are given in Table 8. Adding the allogenic lymphocytes in high concentrations results in a decrease in the yield of the spleen colonies in control, and in the minimum concentration used some increase in the yield of the spleen colonies occurred. The administration of the preparation of the invention reduces both observed deviations as compared to control values if the concentration of introduced cells is not the highest (5×10⁶). Levamisole has identical but a less pronounced effect. Furthermore, in the case when allogenic lymphocytes are not to be added, levamisole somewhat decreases the yield of the spleen colonies, whereas the preparation of the invention does not have such an effect.

TABLE 8

Effect of the Preparation of the Invention and Levamisole on Inactivation of the Stem Cells with Allogenic Lymphocytes

| The preparation | The number of given lymphocytes × $10^6$ | Administration of preparation per os | The counts of spleen endocolonies (M ± m) |
|---|---|---|---|
| Control | 5.0 | — | 0.3 ± 0.1 |
| " | 2.5 | — | 0.9 ± 0.3 |
| " | 1.25 | — | 4.1 ± 0.6 |
| " | — | — | 2.2 ± 0.5 |
| The preparation of the invention | 5.0 | + | 0.3 ± 0.1 |
| The preparation of the invention | 2.5 | + | 1.6 ± 0.2 |
| The preparation of the invention | 1.25 | + | 2.5 ± 0.4 |
| The preparation of the invention | — | + | 2.2 ± 0.4 |
| Levamisole | 5.0 | + | 0.7 ± 0.2 |
| " | 2.5 | + | 1.1 ± 0.2 |
| " | 1.25 | + | 2.3 ± 0.5 |
| " | — | + | 1.1 ± 0.3 |

Thus, administering the preparation of the invention under induced graft versus host reaction conditions normalizes the proliferative activity of target cells and their ability of producing a vital colony, both in case of inhibition (with high lymphocyte concentrations). The preparation of the invention by its efficacy is superior over a known drug levamisole.

The effects of the preparation of the invention as an immunopotentiator on the development of a transferred tumor, and on thermal skin lesions were studied.

The effect of the preparation of the invention on the development of sarcoma-45 (Rous sarcoma) grafted subcutaneously to the right leg of adult female mice of the Vistar breed was studied. The preparation of the invention was administered peritoneally as a suspension in a 1% starch solution in the dose of 125 mg/kg every day during 5 days two weeks after grafting the tumor. Control animals were given only a starch solution. The dynamic development of the tumor was monitored by intravital measurements of its mass. During a 12 month period of observation the inhibition of the development of tumor was found in the group (10 animals) which were given the preparation of the invention.

Thus the preparation of the invention has the inhibitory effect on the development of a massive tumor induced by grafting, probably, via the activation of immunological reactivity.

The results of experiments are given in Table 9.

The study of the effect of the preparation according to the invention on a thermal skin lesion revealed the ability of the preparation to exert a thermoprotective action and reduce a thermal skin lesion.

The effect of the preparation according to the invention on an immunological human status was studied.

Healthy human young volunteers, at the age of 18 to 30 (25 individuals) were under observation.

The immunological status was evaluated on the basis of T-cellular immunity analysis: the state of lymphocytes in the blood of the peripheral vessels, an absolute and relative count of T-cell by Jondal, the state of receptor stability on the outer lymphocyte membrane.

TABLE 9

Effect of the Preparation of the Invention (125 mg/kg daily during 5 days) on the Development of Sarcoma-45 in Rats

| Time after grafting the tumor | Sarcoma growth, $cm^3$ | | |
|---|---|---|---|
| | without the preparation of the invention | administration of the preparation of the invention | |
| 1 month | 11.9 ± 0.86 | 8.2 ± 1.4 | $p < 0.05$ |
| 1 month 10 days | 35.0 ± 3.4 | 21.0 ± 3.9 | $p < 0.05$ |
| 1 month 16 days | 59.8 ± 5.0 | 38.0 ± 7.5 | $p < 0.05$ |
| 2 months | 70.1 ± 2.6 | 39.9 ± 9.7 | $p < 0.05$) |

Using different doses of the preparation of the invention an immunological status was checked in healthy young human beings without a preliminary antigenic enhancement and under vaccinal influenza conditions produced by immunizing them intravenously with influenza A virus vaccine in a 1:1 dilutions in 1 ml.

The experiment was performed by using a double blind method wherein together with tablets of the preparation of the invention, each of 100 mg, an appropriate placebo was used. The results were statistically handled.

The data obtained show that the preparation of the invention in a single per os administration of 100 mg and a 300 mg daily (100 mg three times a day) fails to change the counts of T-populations, but leads to changes in bonding receptors with the outer lymphocyte membrane, which persisted during 14 days (the time of observation).

The vaccination which was performed 24 hours after administering the preparation of the invention had no effect on the nature of changes of bonding receptors with lymphocyte membranes.

The change in the surface properties of lymphocyte membranes under the action of the preparation of the invention is likely to result in changes in functional properties of these cells leading to enhancment of function of the immunity system, which is evidenced by observed protective effect against the development of influenza virus infections. The preparation of the invention prevents from post-influenzal complications, and considerably decreases the frequency of chronic disease exacerbations in persons which had an influenza virus infection.

The results of the clinical trials show that the preparation of the invention is non-toxic, is well tolerated by patients, has the therapeutical effect on influenza A/B virus infections, prevents from the development of post-influenzal complications and chronic disease exacerbations after influenza virus infections. In addition, the preparation of the invention is an efficient interferonogene and immunopotentiator having neither toxic nor side effects on the body. The preparation of the invention may be preferably used as an immunopotentiator in secondary immunodeficiency conditions including radiation and thermoradiation in the treatment of oncologic (tumor) patients, and in chronic and relapsing virus infections.

The preparation of the invention is preferably used 1-2 times a week during the whole course of a specific antineoplastic therapy. A single dose is in the range of 300 to 400 mg (about of 250 mg/$m^2$), a therapeutic dose per course (a curattive course of tumor patients lasts from 1 to 2 months) is of 3 to 6 g of the preparation.

The results of a pharmacokinetic study of a $C^{14}$-labelled preparation of the invention show that the preparation is rapidly evacuated from the body, which allows one to remove all fears against its possible accumulation in the body.

The active principle of the preparation—ethyl 6-bromo-5-hydroxy-4-dimethylaminomethyl-1-methyl-2-phenylthiomethylindole-3-carboxylate hydrochloride monohydrate is prepared as follows.

Ethyl 5-acetoxy-1,2-dimethylindole-3-carboxylate is treated with a brominating agent in an inert organic solvent under reflux.

A brominating agent is preferably bromine or N-bromo-succinimide, and an organic solvent is chloroform, dichloroethane or tetrachloromethane. The resultant ethyl 5-acetoxy-6-bromo-2-bromomethyl-1-methylindole-3-carboxylate is reacted with thiophenol in the presence of an alkali metal hydroxide or its alcoholate in an organic solvent.

An alkali metal hydroxide is potassium hydroxide, sodium hydroxide or the reaction is carried out in the presence of sodium alcoholate. At this stage an organic solvent is preferably methanol, ethanol or isopropanol.

The resultant ethyl 6-bromo-5-hydroxy-1-methyl-2-phenylthiomethylindole-3-carboxylate is reacted with an aminomethylating agent (bis-dimethyl aminomethane or a mixture containing dimethylamine and formaline) in an organic solvent at a temperature ranging from 65° C. to a temperature of refluxing the reaction mixture.

The aminomethylation reaction using bis-dimethylaminomethane is preferably carried out in dioxane under reflux. The yield of ethyl 6-bromo-5-hydroxy-4-dimethylaminomethyl-1-methyl-2-phenylthiomethylindole-3-carboxylate is 70%.

In using the mixture of dimethylamine and formaline for aminomethylation, an organic solvent is preferably acetic acid, and the reaction is carried out at a temperature of 65° to 75° C. Lowering the reaction temperature decelerates aminomethylation, increasing it results in gumming of the reaction mass. At this stage the yield of ethyl 6-bromo-5-hydroxy-4-dimethylaminomethyl-1-methyl-2-phenylthiomethylindole-3-carboxylate is 85%.

The end product is isolated by adding an etheral solution of hydrogen chloride to a solution of the base obtained in acetone. The isolation of the end product is preferably carried out by treating the resultant base with hydrochloric acid in acetone under reflux. The process is carried out according to the following reaction scheme:

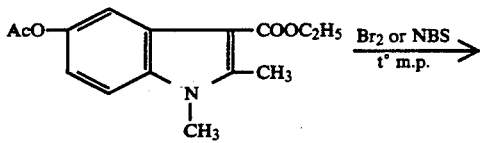

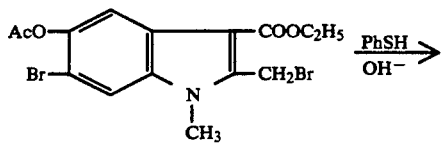

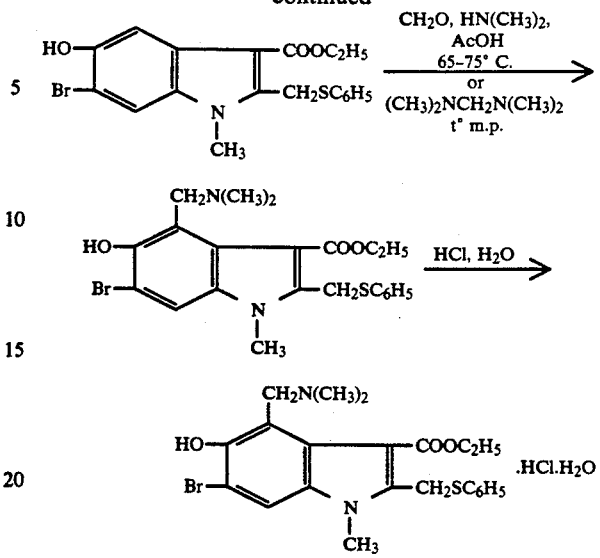

For a better understanding the present invention, the following examples of a process for preparing the compound according to the invention will be given below.

EXAMPLE 1

To a solution containing ethyl 5-acetoxy-1,2-dimethylindole-3-carboxylate (110 g, 0.4 mole) in 1200 ml of tetrachloromethane was added bromine (127.8 g, 0.8 mole) under stirring and reflux. The reaction was cooled, and the precipitate was removed by filtration.

150.7 g (87%) of ethyl 5-acetoxy-6-bromo-2-bromomethyl-1-methylindole-3-carboxylate was obtained in the form of a white crystalline powder, soluble under heating in a low alcohol, carbon dichloride, and non-soluble in water; m.p. 179°–180° C.

Elemental Analysis for $C_{15}H_{15}BrNO_4$: Found, % C, 41.50; H, 3.50; Br, 36.97. Calculated, %: C, 41.60; H, 3.49; Br, 36.90.

To a solution containing potassium hydroxyde (52.1 g, 0.93 mole) in 1300 ml of methanol at room temperature was added thiophenol (34.1 g, 0.31 mole) under stirring and then ethyl 5-acetoxy-6-bromo-2-bromomethyl-1-methylindole-3-carboxylate (135 g, 0.31 mole) was also added.

The mixture was allowed to stay at room temperature for 3 hours followed by neutralizing (acidifying off) with a diluted acetic acid. The precipitate was filtered off and washed with water.

125.6 g (96.4%) of ethyl 6-bromo-5-hydroxy-1-methyl-2-phenylthiomethylindole-3-carboxylate was obtained as a yellow crystalline powder, under heating in a low alcoholate, ethylacetate, and non-soluble in water, m.p. 196°–197° C. (from ethylacetate).

Elemental Analysis for: $C_{19}H_{18}BrNO_3S$: Found, %: C, 54.14; H, 4.24. Calculated, %: C, 54.30; H, 4.32.

To 125 ml of acetic acid was added a 33% solution of dimethylamine (56 ml, 0.385 mole) under stirring and cooling and then a 37.7% solution of formaline (12.6 ml, 0.165 mole) was added. To the resultant solution was added ethyl 6-bromo-5-hydroxy-1-methyl-2-phenylthiomethylindole-3-carboxylate (61.3 g, 0.146 mole). The reaction mixture was stirred at a temperature in the range of 65° to 75° C. for 30 minutes. The resultant solution was cooled and neutralized with a solution of potassium hydroxide. The precipitate was removed and washed with water.

59.9 g (85.1%) of ethyl 6-bromo-5-hydroxy-4-dimethylaminomethyl-1-methyl-2-phenylthiomethylindole-3-carboxylate was obtained as a white crystalline solid, soluble under heating in acetone, acetonitrile, dioxane, a low alcohol and non-soluble in water, m.p. 127°–128° C. (from acetonitrile).

Elemental Analysis for: $C_{22}H_{25}BrN_2O_3S$: Found, %: C, 55.53; H, 5.35; N, 6.01. Calculated, %: C, 55.34; H, 5.29; N, 5.87.

To a solution containing ethyl 6-bromo-5-hydroxy-4-dimethylaminomethyl-1-methyl-2-phenylthiomethylindole-3-carboxylate (47.1 g, 0.0986 mole) in 280 ml of acetone a concentrated hydrochloric acid solution (11 ml, 0.1282 mole) under stirring and refluxing was added. The reaction mixture was cooled, the precipitate was removed and recrystallized from a mixture of acetone and ethanol.

45.1 g (86%) of the end product—ethyl 6-bromo-5-hydroxy-4-dimethylaminomethyl-1-methyl-2-phenyl-thiomethylindole-3-carboxylate hydrochloride monohydrate was obtained.

Elemental Analysis for: $C_{22}H_{28}BrClN_2O_4S$: Found, %: C, 49.57; H, 5.30; Br, 14.98; Cl, 6.54; S, 5.89; N, 5.30; $H_2O$, 3.28. Calculated, %: C, 49.67; H, 5.31; Br, 15.02; C, 6.67; N, 5.27; S, 6.03; $H_2O$, 3.38.

The yield of the end product based on the starting ethyl 5-acetoxy-1,2-dimethylindole-3-carboxylate is of 61.38%.

EXAMPLE 2

The process was carried out in a manner described in Example 1, but for preparing ethyl 5-acetoxy-6-bromo-2-bromomethyl-1-methylindole-3-carboxylate the reaction was carried out in chloroform, with the product being isolated at a 79.3% yield; m.p. 167°–169° C.

The yield of the end product was 55.95% based on ethyl 5-acetoxy-1,2-dimethylindole-3-carboxylate. The product was identical to that of Example 1.

EXAMPLE 3

The process was carried out in a manner described in Example 1, but for preparing ethyl 5-acetoxy-6-bromo-2-bromomethyl-1-methylindole-3-carboxylate, the reaction was carried out in dichloroethane, the product being isolated at a 63.5% yield; m.p. 167°–168° C.

The yield of the end product was 46.07% based on ethyl 5-acetoxy-1,2-dimethylindole-3-carboxylate.

The product was similar to that of Example 1.

EXAMPLE 4

To a solution, containing ethyl 5-acetoxy-1,2-dimethylindole-3-carboxylate (44 g, 0.16 mole) in 560 ml of tetrachloromethane was added dropwise N-bromosuccinimide (64 g, 0.36 mole), and the reaction mixture was refluxed for 6 hours. Succinimide was filtered off the hot solution, washed with hot tetrachloromethane. After partial evaporation of the filtrate in vacuum followed by cooling, the precipitate was removed and recrystallized from isopropanol, 43.4 g (62.7%) of ethyl 5-acetoxy-6-bromo-2-bromomethyl-1-methylindole-3-carboxylate, m.p. 179°–180° C. were obtained.

The process was further carried out in a manner described in Example 1. The yield of the end product was 44.24%, the product was identical to that of Example 1.

EXAMPLE 5

The process was carried out in a manner described in Example 1, but for preparing ethyl 6-bromo-5-hydroxy-4-dimethylaminomethyl-1-methyl-2-phenylthiomethylindole-3-carboxylate, the aminomethylation reaction was accomplished as follows.

To a solution containing ethyl 6-bromo-5-hydroxy-1-methyl-2-phenylthiomethylindole-3-carboxylate (76.4 g, 0.18 mole) in 470 ml of diowane was added bis-dimethylaminomethane (50 ml, 0.36 mole). The reaction mixture was refluxed for 3 hours, cooled, diluted with a 3–4-fold amount of water. The precipitated crystalls were removed, washed with water and dried to give 60.1 g (70%) of ethyl 6-bromo-5-hydroxy-4-dimethylaminomethyl-1-methyl-2-phenylthiomethylindole-3-carboxilate; m.p. 125°–126° C.

The process was further carried out similarly to Example 1.

The yield of the end product was 50.49% based on the starting ethyl 5-acetoxy-1,2-dimethylindole-3-carboxylate. The product was similar to that of Example 1.

EXAMPLE 6

The process was accomplished in a manner described in Example 1, but for preparing ethyl 6-bromo-5-hydroxy-1-methyl-2-phenylthiomethilindole-3-carboxylate the reaction was carried out in ethanol in the presence of sodium ethoxide. The product was isolated, giving the of a 96.8% yield, m.p. 196°–197° C.

The yield of the end product based on the starting ethyl 5-acetoxy-1,2-dimethylindole-3-carboxylate was 59.4%.

EXAMPLE 7

The process was carried out in a manner to that of Example 1, but for preparing ethyl 6-bromo-5-hydroxy-1-methyl-2-phenylthiomethylindole-3-carboxylate, the reaction was carried out in isopropanol in the presence of sodium hydroxide. The product was isolated at a yield of 94.5%, m.p. 196°–197° C.

The yield of the end product on the starting ethyl 5-acetoxy-1,2-dimethylindole-3-carboxylate was 56.7%.

INDUSTRIAL APPLICABILITY

The compound of the invention—ethyl 6-bromo-5-hydroxy-4-dimethylaminomethyl-1-methyl-2-phenyl-thiomethylindole-3-carboxylate hydrochloride monohydrate has antiviral, interferon-inducing and immunomodulatory effects and is an active principle of the preparation having the antiviral, interferon-inducing and immunomodulatory effects.

We claim:

1. Ethyl-6-bromo-5-hydroxy-4-dimethylaminomethyl-1-methyl-2-phenylthiomethylindole-3-carboxymate hydrochloride monohydrate of the following formula:

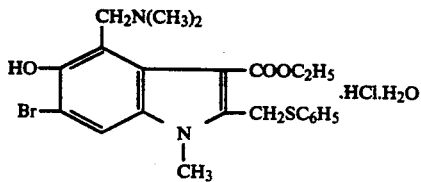

2. A process for preparing ethyl-6-bromo-5-hydroxy-4-dimethylaminomethyl-1-methyl-2-phenylthiomethylindole-3-carboxylate hydrochloride monohydrate according to claim 1, which comprises treating ethyl-5-acetoxy-1,2-dimethylindole-3-carboxylate with a brominating agent in an inert solvent under reflux, reacting the resultant ethyl-5-acetoxy-6-bromo-2-bromomethyl-1-methylindole-3-carboxylate with thiophenol in the presence of an alkali metal hyroxide or its alcoholate in an organic solvent, reacting the resultant ethyl 6-bromo-5-hydroxy-1-methyl-2-phenylthiomethylindole-3-carboxylate with an aminomethylating agent in an organic solvent at a temperature from 65° C. to the temperature of refluxing the reaction mixture, with subsequent isolation of the end product from the resultant base—ethyl 6-bromo-5-hydroxy-4-dimethylaminoethyl-1-methyl-2-phenylthiomethylindole-3-carboxylate.

3. A process according to claim 2, wherein the brominating agent is bromine or N-bromosuccinimide.

4. A process according to claim 2, wherein the inert organic solvent is chloroform, dichloroethane or tetrachloromethane.

5. A process according to claim 2 which comprises reacting ethyl 5-acetoxy-6-bromo-2-bromomethyl-1-methylindole-3-carboxylate with thiophenyl, and wherein the organic solvent is methanol, ethanol or isopropanol.

6. A process according to claim 2, wherein the aminomethylating agent is a mixture containing dimethylamine and formaline, or bis-dimethylaminomethane.

7. A process according to claim 6, wherein in using a mixture consisting of dimethylamine and formaline, the organic solvent is acetic acid, and the aminomethylation is carried out at a temperature in the range of 65° to 75° C.

8. A process according to claim 6, wherein in using bis-dimethylaminomethane, the organic solvent is dioxane, and the aminomethylation is carried out at the temperature of reflux of the reaction mixture.

9. A process according to claim 2, wherein the isolation of the end product is accomplished by treating ethyl 6-bromo-5-hydroxy-4-dimethylaminomethyl-1-methyl-2-phenylthiomethylindole-3-carboxylate with hydrochloric acid in acetone under reflux.

10. A pharmaceutical preparation having the antiviral, interferon-inducing and immunomodulatory effects consisting of an active principle and a pharmaceutically acceptable carrier, wherein the active principle is ethyl 6-bromo-5-hydroxy-4-dimethylaminomethyl-1-methyl-2-phenylthiomethylindole-3-carboxylate hydrochloride monohydrate according to claim 1.

11. A pharmaceutical preparation according to claim 10, which contains an active principle in an amount of 0.1 to 0.2 g per 1 tablet.

12. A pharmaceutical preparation according to claim 11, wherein the pharmaceutically acceptable carrier is an excipient—starch or castor sugar.

* * * * *